United States Patent
Ramsey et al.

[11] Patent Number: 6,056,859
[45] Date of Patent: May 2, 2000

[54] METHOD AND APPARATUS FOR STAINING IMMOBILIZED NUCLEIC ACIDS

[75] Inventors: J. Michael Ramsey, Knoxville; Robert S. Foote, Oak Ridge; Stephen C. Jacobson, Knoxville, all of Tenn.

[73] Assignee: Lockheed Martin Energy Research Corporation, Oak Ridge, Tenn.

[21] Appl. No.: 08/800,241

[22] Filed: Feb. 12, 1997

[51] Int. Cl.$^7$ .................................................. G01N 27/26
[52] U.S. Cl. ........................ 204/451; 204/452; 204/453; 204/601; 204/603; 204/604; 435/287.2; 435/6; 422/68.1
[58] Field of Search .................................. 204/450, 451, 204/452, 453, 600, 601, 603; 435/297.2, 6; 422/68.1, 100, 102

[56] References Cited

U.S. PATENT DOCUMENTS

| | | |
|---|---|---|
| 4,908,112 | 3/1990 | Pace . |
| 5,073,239 | 12/1991 | Hjerten . |
| 5,092,973 | 3/1992 | Zare et al. . |
| 5,110,431 | 5/1992 | Moring . |
| 5,126,022 | 6/1992 | Soan et al. . |
| 5,132,012 | 7/1992 | Miura et al. . |
| 5,141,621 | 8/1992 | Zare et al. . |
| 5,180,480 | 1/1993 | Manz . |
| 5,250,263 | 10/1993 | Manz . |
| 5,296,114 | 3/1994 | Manz . |
| 5,376,252 | 12/1994 | Ekström et al. . |
| 5,585,069 | 12/1996 | Zanzucchi et al. . |
| 5,603,351 | 2/1997 | Cherukuri et al. . |
| 5,605,662 | 2/1997 | Heller et al. . |
| 5,632,876 | 5/1997 | Zanzucchi et al. . |
| 5,637,469 | 6/1997 | Wilding et al. . |
| 5,653,939 | 8/1997 | Hollis et al. . |
| 5,661,028 | 8/1997 | Foote . |
| 5,716,825 | 2/1998 | Hancock et al. . |
| 5,759,779 | 6/1998 | Dehlinger . |
| 5,804,384 | 9/1998 | Muller et al. . |
| 5,858,195 | 1/1999 | Ramsey . |

FOREIGN PATENT DOCUMENTS

| | | |
|---|---|---|
| 0 356 160 A2 | 2/1990 | European Pat. Off. . |
| 0 620 432 A1 | 4/1993 | European Pat. Off. . |
| 2 191 110 | 12/1987 | United Kingdom . |
| 94/05414 | 3/1994 | WIPO . |
| 95/12808 | 5/1995 | WIPO . |

OTHER PUBLICATIONS

Wilding et al., "Manipulation and Flow of Biological Fluids in Straight Channels Micromachined in Silicon", Clinical Chem., vol. 40, No. 1, 1994.

Wilding et al., "PCR in a Silicon Microstructure", Clinical Chemistry, vol. 40, No. 9, 1994.

Dasgupta et al., "Electroosmosis: A Reliable Fluid Propulsion System for Flow Injection Analysis", Analytical Chemistry, vol. 66, No. 11, Jun. 1, 1994.

(List continued on next page.)

*Primary Examiner*—William H. Beisner
*Attorney, Agent, or Firm*—Dann, Dorfman, Herrell and Skillman

[57] ABSTRACT

A method for staining immobilized nucleic acids includes the steps of affixing DNA probes to a solid substrate, moving target DNA material into proximity with the DNA probes, whereby the target DNA hybridized with specific ones of the DNA probes, and moving a fluorescent dye into proximity with the hybridized target DNA, whereby the fluorescent dye binds to the hybridized DNA to enable subsequent detection of fluorescence.

41 Claims, 5 Drawing Sheets

OTHER PUBLICATIONS

Science • vol. 261 • Aug. 13, 1993 entitled: Micromachining a Miniaturized Capillary Electrophoresis–Based Chemical Analysis System on a Chip, by D. Jed Harrison, Karl Fluri, Kurt Seiler, Zhonghui Fan, Carlo S. Effenhauser, and Andreas Manz.

D. Jed Harrison, Andreas Manz, Zhonghui Fan, Hans Lüdi, and H. Michael Widmer, "Capillary Electrophoresis and Sample Injections Systems Integrated on a Planar Glass Chip" Analytical Chemistry, vol. 64, No. 17 (Sep. 1, 1992) 1926–1932.

Carlo S. Effenhauser, Andreas Manz, and H. Michael Widmer, "Glass Chips for High Speed Capillary Electrophoresis Separations with Submicrometer Plate Heights" Analytical Chemistry, vol. 65, No. 19 (Oct. 1, 1993) 2637–2642.

M. Deml, F. Foret, and P. Boček, "Electric Sample Splitter for Capillary Electrophoresis" Journal of Chromatography, 320 (1985) 159–165.

METHOD AND APPARATUS FOR STAINING IMMOBILIZED NUCLEIC ACIDS

This invention was made with government support under Contract No. DE-AC05-84OR21400 awarded by the U.S. Department of Energy to Lockheed Martin Energy Systems, Inc. and the government has certain rights in this invention.

BACKGROUND OF THE INVENTION

1. Field of the Invention

The present invention relates generally to medical and/or biological testing and devices for performing same, and more particularly, to a method and apparatus for fluorescently staining immobilized nucleic acids. Fluorescent dyes are used which specifically bind to double-strand nucleic acids and/or which have detectably altered fluorescent properties when bound to such strands. Target nucleic acids are detected when hybridized to arrays of single-strand nucleic acid probes immobilized to solid substrates.

2. Description of the Related Art

Techniques for isolating and identifying genes and gene fragments and performing DNA sequencing are now in wide use. For example, in one technique, genomic DNA is digested with restriction enzymes, and then electrophoresed through agarose gels, and then blotted to GeneScreen (DuPont) utilizing standard procedures. Radiolabeled hybridization probes are prepared with the random hexamer labeling techniques described by Feinberg and Bogelstein (*Analytical Biochemistry*, 137:226–267,1984).

It is generally known how to use arrays of oligonucleotide probes to analyze target nucleic acids for specific nucleotide sequences by hybridization of the target to complementary probes in the array. The detection of hybridized sequences has typically involved pre-labeling the target nucleic acid with a fluorescent, radioactive or other detectable label in a time consuming step requiring expensive reagents.

The adsorption of non-hybridized, labeled nucleic acids to the array substrate can also result in high background signals which lower the sensitivity of hybridization detection.

Thus, a continuing need exists for methods and apparatuses that avoid the use of expensive reagents, while simplifying the overall procedures to require smaller samples and fewer processing steps.

SUMMARY OF THE INVENTION

An object of the present invention is to provide a method and apparatus for staining immobilized nucleic acids that obviates the need to pre-label the target nucleic acid with a fluorescent, radioactive or other labeling substance. Another object of the present invention is to provide a method and apparatus for staining immobilized nucleic acids that reduces the number of processing steps and the number and type of reagents, thus making the process more economically practical.

Another object of the present invention is to provide a method and apparatus for staining immobilized nucleic acids which reduces or eliminates background fluorescence from non-hybridized, labeled target sequences, thus allowing greater sensitivity of detection.

These and other objects are met by providing a method which includes the steps of affixing DNA probes in a channel of a microchip structure, moving target DNA material into proximity with the DNA probes, whereby the target DNA hybridizes with specific ones of the DNA probes, moving a fluorescent dye into proximity with the hybridized target DNA, whereby the fluorescent dye binds to the hybridized DNA, and detecting the fluorescence of the hybridized, dye stained DNA. A washing step can also be included between the dye labeling and fluorescence detection steps to decrease the background signals and improve detection.

These together with other objects and advantages which will be subsequently apparent, reside in the details of construction and operation as more fully hereinafter described and claimed, with reference being had to the accompanying drawings forming a part hereof, wherein like numerals refer to like elements throughout.

DETAILED DESCRIPTION OF THE PREFERRED EMBODIMENTS

Figure 1:
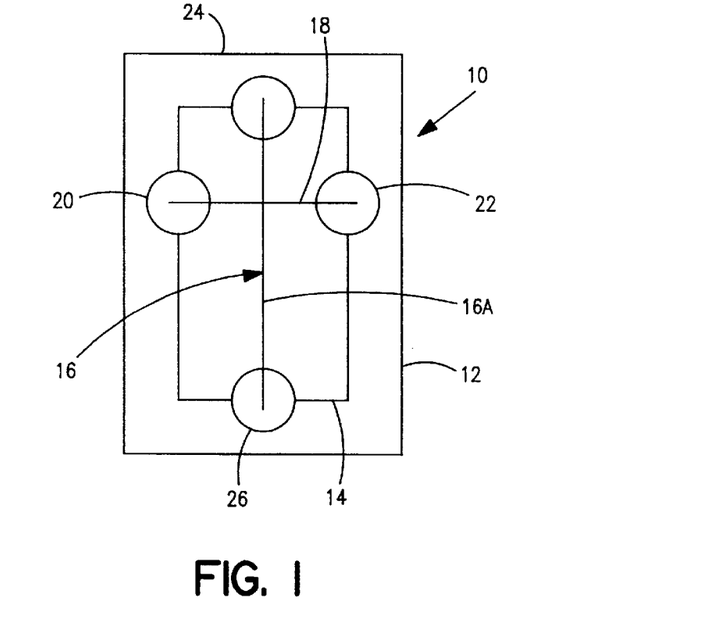
FIG. 1 is a top view of a microchip structure used to stain immobilized nucleic acids according to the present invention.

Referring to FIG. 1, a microchip 10 includes a glass substrate 12 and a cover plate 14 which covers a microchannel structure formed in the upper surface of the substrate 12. The cover plate 14 is permanently bonded to the substrate 12. Both the substrate 12 and cover plate 14 are preferably made of clear glass, and the substrate may preferably be made from a standard microscope slide.

The microchannel structure is formed using standard photolithographic techniques, and includes a first channel 16 and a second channel 18 which intersects with the first channel. A plurality of reservoirs 20, 22, 24 and 26 are bonded to the substrate over the terminal ends of the channels, which then act as "ports" for the introduction of material contained in the reservoirs into the channels.

Materials are moved through the microchannel structure to perform the methods described below by either hydraulic or electrokinetic means. In the former, a vacuum could be applied to one of the reservoirs, capping two others, and leaving the fourth open to the atmosphere. Other hydraulic configurations could be employed. Alternatively, the materials could be moved by applying electric fields to the material in the reservoirs to impart electroosmotic or electrophoretic movement. Such electrokinetic techniques are described in co-pending application Ser. No. 08/283,769, filed Aug. 1, 1994, which is incorporated herein by reference.

The methods of the present invention entail utilizing the microchip described above to perform a variety of biological, genetic, immunological, or other medical or chemical tests. In one method, fluorescent dyes are used which specifically bind to double-strand nucleic acids and/or which have detectably altered fluorescent properties when bound to such strands. These dyes bind to the duplex DNA region produced by hybridization of the target DNA to the probe, as shown in FIG. 2A.

Figure 2A:
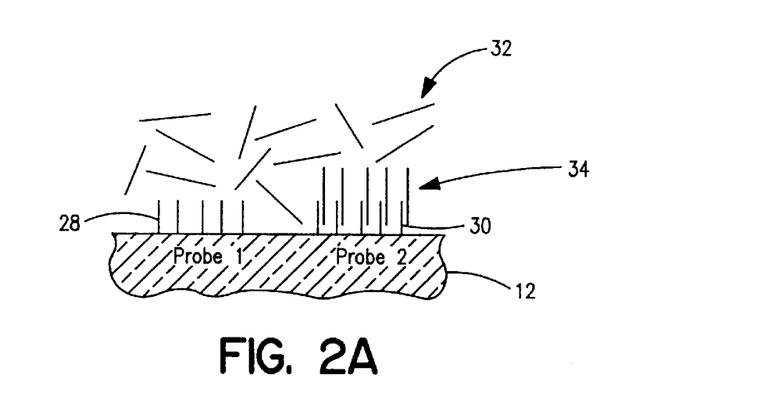
FIGS. 2A and 2B are enlarged, schematic views showing (A) sequence-specific DNA hybridization and (B) fluorescence staining of dsDNA.
Figure 2B:
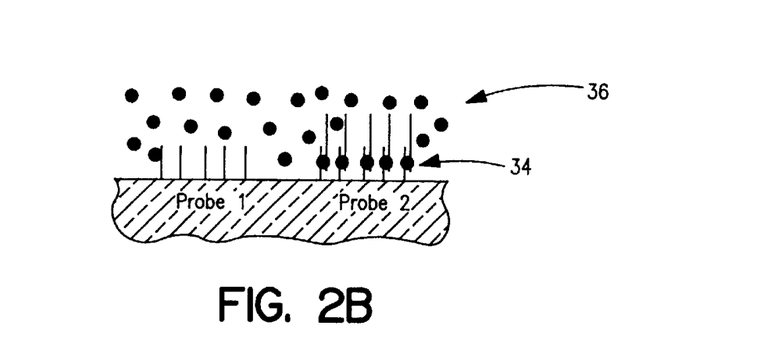

Referring to FIG. 2A, and according to the present invention, DNA probes 28 and 30 (shown as different groups, "Group 1" and "Group 2") are affixed to the surface of the substrate 12 in one of the channels. Preferably, and referring to FIG. 1, the probes are affixed in the channel 16 below the intersection with channel 18. DNA fragments 32, in solution, are moved into proximity with the probes 28 and 30 by either hydraulic or electrokinetic means. In a particularly preferred embodiment the DNA fragments in solution are placed in reservoir 20 and a buffer solution is placed in the reservoir 24.

Application of electric fields or hydraulic pressure cause movement of the fragments through the channel 18, through the intersection with channel 16, and downwardly into the section 16A of the channel 16 which extends between the intersection and the waste reservoir 26. It is in this section 16A that the probes 28 and 30 are located. In general, the field is established such that the waste reservoir 26 is at a lower electric or hydraulic potential than that which is applied to the other reservoirs. In all cases where the electrokinetic of hydraulic transport is utilized, the potential energy gradient is controlled such as to transport the necessary materials to the proper locations. Once the fragments have been transported to the section 16A of channel 16, the means of transport may be temporarily discontinued while hybridization proceeds.

The DNA fragments 32 will hybridize with probes of complementary sequence, of which only two are illustrated in FIG. 2A. As seen in FIG. 2A, the DNA fragments attach to Probe 2-type probes to form hybridized target DNA 34. Next, the staining step takes place by moving dsDNA-specific fluorescent dye 36 (shown as black dots) into proximity with the hybridized target DNA, where the dye becomes bound to the DNA as shown. This movement can be done hydraulically or electrokinetically. In either case, the dye solution is placed in reservoir 22 and is caused to move into proximity with the hybridized target DNA in channel section 16A. For electrokinetic motion, this is accomplished by applying an electric field to the reservoirs to impart motion of the dye molecules, or solution containing same, through channel 18 and into channel section 16A below the intersection.

Figure 3A:
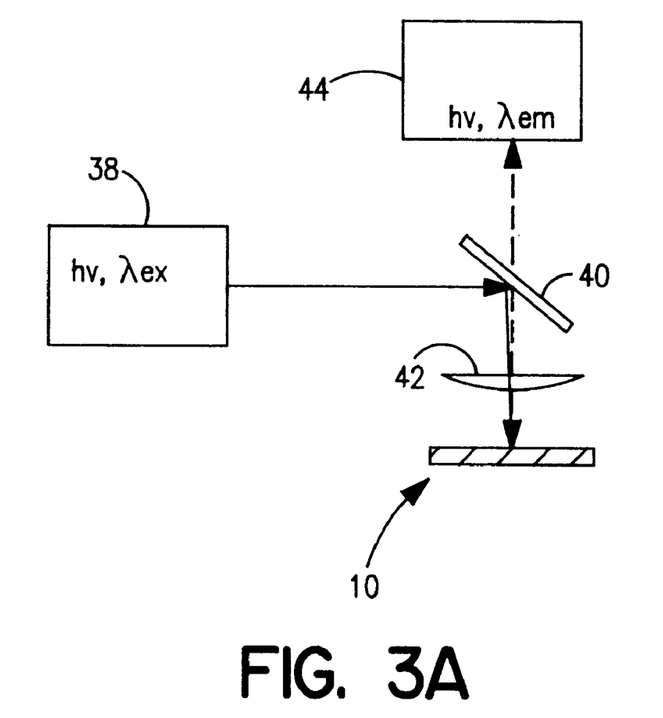
FIG. 3A is a schematic view of an apparatus for detecting fluorescence in hybridized probes.
Figure 3B:
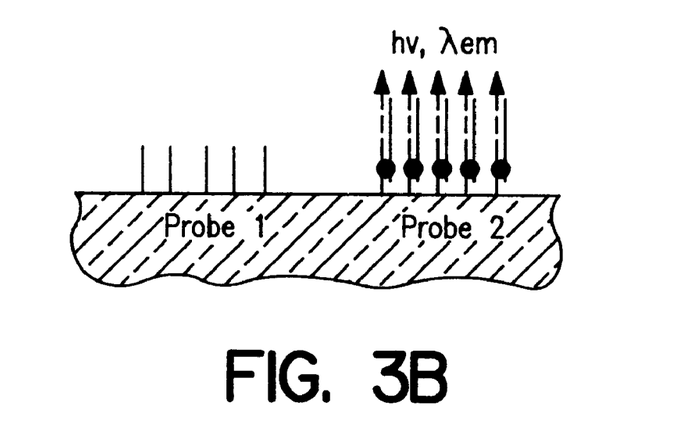
FIG. 3B is an enlarged view of the microchip with a light source focused on the hybridized probes for detecting fluorescence.

After staining, the fluorescence of the hybridized probes can be detected with an apparatus shown in FIG. 3a, in which a light source, such as a laser 38, outputs a beam of light at an excitation wavelength, $\lambda_{ex}$, which is directed by a mirror 40 through lens 42 onto the microchip 10 in the vicinity of the dyed hybridized target DNA. The emission radiation, at wavelength, $\lambda_{em}$, is detected with a detector 44. The emission radiation is illustrated schematically in FIG. 3B.

Figure 4A:
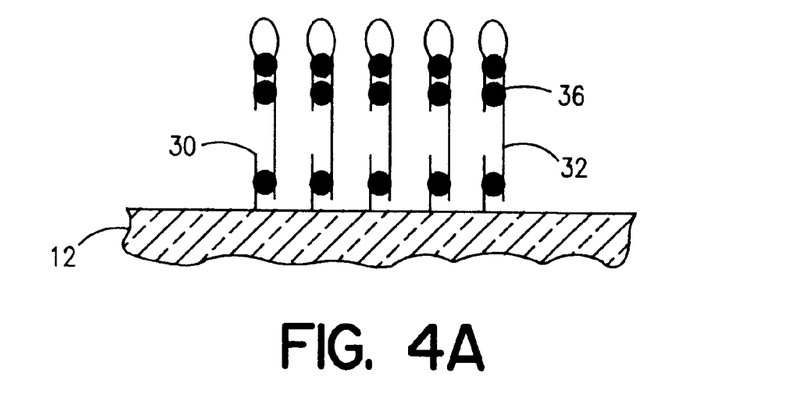
FIGS. 4A, 4B and 4C are schematic illustrations of the effects of duplex sequences in target and probe nucleic acids on dye binding.
Figure 4B:
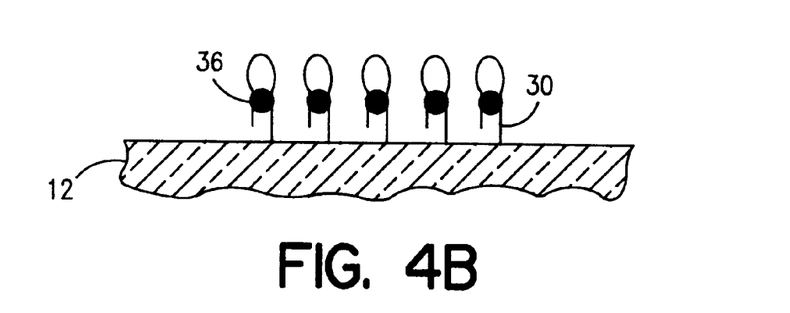
Figure 4C:
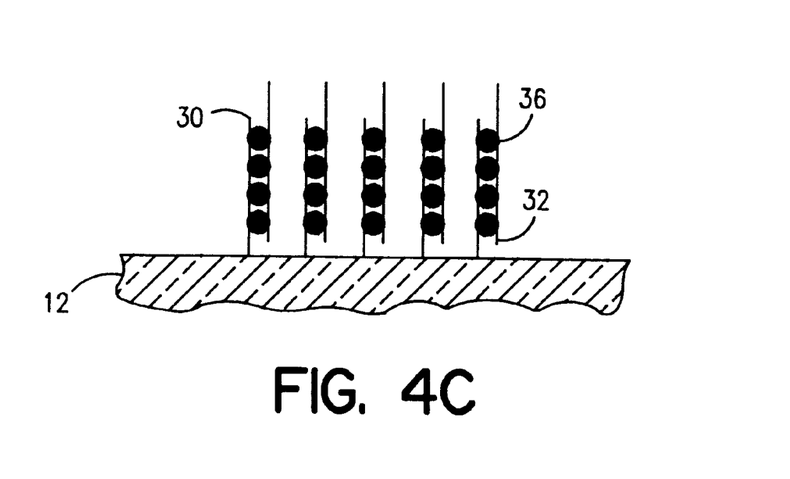

The dye may also bind to double-stranded regions in the target DNA itself, which should further enhance fluorescence signals from hybridized probe sites, as seen in FIG. 4A. Probe sequences containing self-complementary regions could also bind the dye, resulting in false positive hybridizations as seen in FIG. 4B. Such probes would not normally be used in hybridization arrays. In any case, because the number of bound dye molecules is dependent on the length of the duplex region, signals due to self-complementary regions in the probe could be quantitatively distinguished from those due to hybridization to target DNA, which produces longer duplex regions, as seen in FIG. 4C. Comparison of array signals produced by dye treatment before and after target hybridization could therefore be used to eliminate false positive sequence identifications.

For the purposes of illustration, and not limitation, the hybridization of target to probe in FIGS. 2A,2B,4A and 4C is shown as occurring at the ends of the target sequence; however, the probe can hybridize to a complementary sequence anywhere within the target nucleic acid. Likewise, the hairpin structures shown at the ends of the target nucleic acids in FIG. 4A could also occur at an internal target sequence.

A large number of fluorescent dyes have been developed for staining nucleic acids (cf. A. S. Waggoner in *Applications Of Fluorescence In The Biomedical Sciences*, ed. by D. L. Taylor et al., Alan R. Liss, Inc. 1986, pp. 3–28). These dyes bind non-covalently with nucleic acids by intercalation between the base parts and/or by electrostatic interactions with the negatively charged phosphate groups. The dyes most suitable for detection of target DNA hybridization to DNA probe arrays are those which bind with high affinity to dsDNA, have little or no affinity for single-stranded DNA, and/or undergo a large intensity enhancement or wavelength shift in fluorescence when bound to dsDNA.

The classic fluorescent stain for nucleic acids is ethidium bromide. At high salt concentrations this dye binds to double-stranded DNA, RNA, or DNA-RNA hybrids with little or no binding to single-stranded polynucleotides. Fluorescence of the dye ($\lambda_{em}$ 590 nm) is enhanced by >20-fold on binding to the duplex nucleic acids.

Other useful nucleic acid stains include propidium iodide, acridine orange, DAPI (4',6-diamidino-2-phenylindole), anthracyclines, actinomycins, mithramycins and certain Hoechst (bisbenzimide) dyes. Acridine orange fluoresces at longer wavelength when bound to single-stranded RNA than when bound to dsDNA, and can be used to distinguish the two types of nucleic acid.

In addition to these well-known dyes, several newer nucleic acid stains are commercially available with improved binding and/or fluorescence characteristics. Two newer dyes, TOTO-a (a benzothiazolium-4- quinolinium dimer) and PicoGreen (a dsDNA-specific dye from Molecular Probes, Inc.) have been tested and found to be suitable for the detection of hybridized DNA probes on glass substrates.

Figure 5:
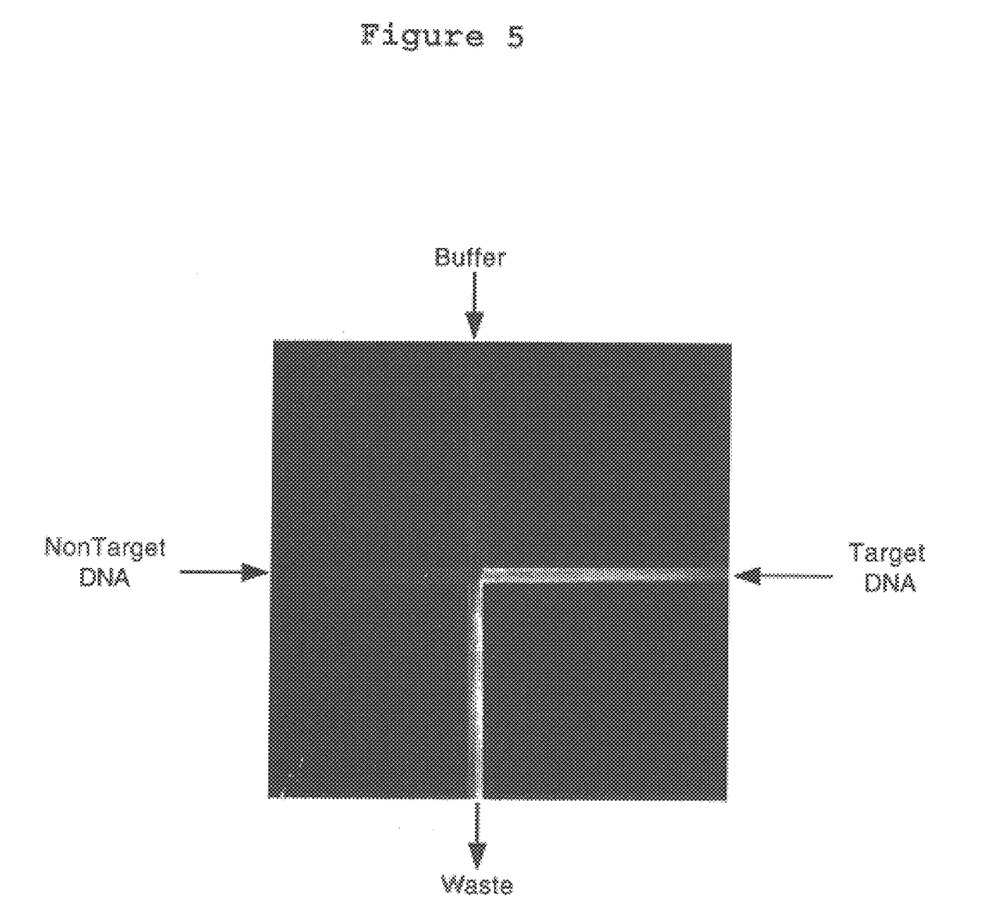
FIG. 5 is a CCD image of a test cross-channel microchip used for fluorescent staining according to the present invention.

The utility of post-hybridization fluorescence staining has been demonstrated in experiments using microchannel devices, such as the cross-channel device shown in FIG. 1. A CCD image (512×512 pixels) is shown in FIG. 5. The channels of this device were uniformly derivatized with a 16-mer DNA probe as described in co-pending application no. entitled "Method and Apparatus for Analyzing Nucleic Acids," which is incorporated herein by reference. A complementary 16-mer (T) was added to one arm of the cross-channel in hybridization buffer while a non-complementary 16-mer oligonucleotide (N) was simultaneously added to the opposite arm. A dsDNA-specific fluorescent stain (PicoGreen, Molecular Probes) was then added to all channels and the microdevice was examined by epifluorescence microscopy, producing the CCD image of FIG. 5.

Figure 6:
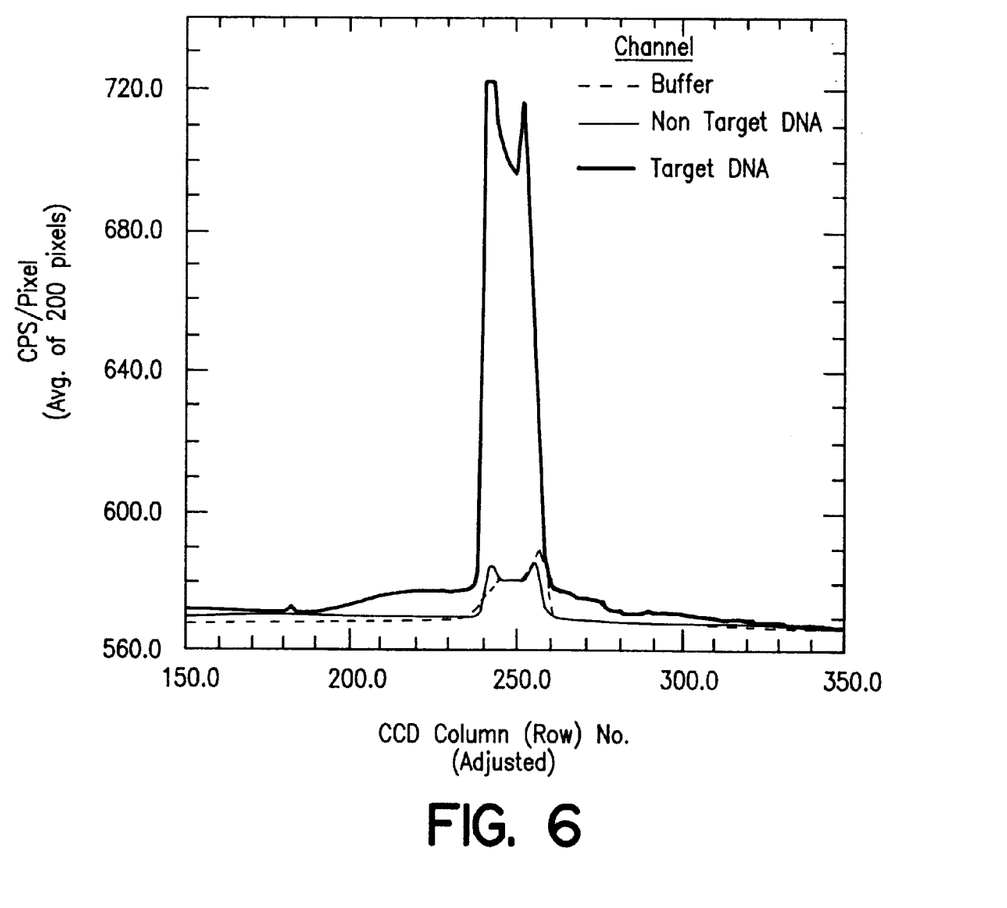
FIG. 6 is a graph comparing target to non-target DNA fluorescence resulting from the test performed in association with FIG. 5.

Channels exposed to the complementary oligonucleotide showed strong fluorescence due to the presence of the probe-target dsDNA, while the fluorescence of the channel exposed to non-complementary DNA was equal to that of the channel exposed only to buffer during the hybridization step and therefore containing only the probe DNA. The contrast between hybridized and non-hybridized channels was approximately 10-fold as indicated in FIG. 6. The epifluorescence microscopy uses an argon ion laser for illumination at 448 nm and 1.0 second CCD exposure. The image was enhanced and analyzed using commercial software (IPLab Spectrum). Each data point in the graph of FIG. 6 is the average counts per second ("cps") of 200 pixels in a row or column parallel to the channel indicated and is uncorrected for the CCD detector's analog-to-digital converter offset of +~560 counts per pixel. Row and column numbers were adjusted to align channel positions.

The substrate and cover plate used to make the microchip are preferably glass, but other solids could be used, such as quartz, silicon, or organic polymeric materials.

In an alternative embodiment of this invention, the nucleic acid analyte and an intercalating dye may be simultaneously moved into proximity with the immobilized oligonucleotide probe. The mobile components may be transported by electrokinetic or hydraulic means. For example, a fluid reservoir containing the analyte may be connected via a fluidic channel containing the immobilized probe or probes to a second reservoir containing a positively charged intercalating dye. An electric potential may then be applied between the two reservoirs such that the negatively charged nucleic acid migrates toward the dye reservoir and the positively charge dye migrates in the counter direction toward the analyte reservoir, both dye and nucleic acid analyte thereby being moved into proximity with the immobilized probes. Alternatively, fluid channels from the analyte and dye reservoirs may be joined at a point upstream from the region containing the immobilized probes and hydraulic means used to move the merged solution stream through the channel containing the probes.

In a further embodiment, the nucleic acid analyte and dye may be pre-mixed in a single reservoir and the resulting solution moved into proximity with the immobilized probes by hydraulic means. A number of variations in channel configurations and transport modes are thereby available for simultaneous addition of the analyte and dye to the region of the apparatus containing the immobilized probes. Potential interference of the intercalating dye with hybridization of analyte to probe may be minimized by appropriate choice of the dye and/or its concentration. Following the combined hybridization and staining step, the probe region may be washed with buffer to remove unbound analyte and dye.

In addition to the detection of DNA target sequences the invention may be used to detect RNA targets. For example, the invention may be used to detect specific messenger RNA (mRNA) sequences, or to identify RNA viruses. A number of dyes, including ethidium bromide, ethidium homodimers and acridine orange, are available for staining RNA.

Single-stranded 2'-deoxyribonucleic acid (DNA) sequences containing eight to twenty-five nucleotides are preferred as nucleic acid probes, although shorter or longer sequences may be used in some instances. Ribonucleic acid (RNA) sequences, as well as a variety of oligonucleotide analogues might also be used as probes. A large number of oligonucleotide analogues have been reviewed in the literature (R. S. Varma, Synlett, No. 9: 621–637, 1993; J. F. Milligan et al., J. Medicinal Chem., 36: 1923–1937, 1993). For example, internucleotide linkages used in backbone-modified oligonucleotides include phosphotriester, phosphorothioate, phosphorodithioate, methylphosphonate, phosphoramidate, carbonate, carboxymethyl, acetamidate, carbamate, peptide, thioether, sulfonate, sulfonamide, sulfamate, sulfide, sulfoxide, sulfone, formacetal, thioformacetal, methylhydroxylamine, N-cyanoguanidine and alkylsilyl linkages. Of particular interest are analogues such as the peptide nucleic acids (PNAs), which have non-charged backbones and form stable heteroduplexes with normal nucleic acids at low ionic strength due to the absence of electrostatic repulsion. This property would allow the use of electroosmotic flow in the microfluidic apparatus to transport target nucleic acids in low ionic strength hybridization buffer. Cationic oligonucleotide analogues could also be useful for this purpose. The binding of cationic oligonucleotides, containing dimethylamino- or morpholino-alkylphosphoramidate internucleotide linkages, to normal complementary oligodeoxynucleotides has been shown to be either independent of salt concentration or to be more stable in the absence of salt, depending on the nature of the aminoalkyl group (R. L. Letsinger et al., J. Am. Chem. Soc. 110: 4470–4471, 1988).

Oligonucleotide analogues with modifications of the sugar or heterocyclic base moieties have also shown enhanced affinities for hybridization with DNA and/or RNA targets and may be useful nucleic acid probes. Oligonucleotides containing 2'-fluoro, 2'-O-methyl and 2'-O-allyl modified sugars have shown enhanced or equal affinity for RNA targets compared to normal oligoribonucleotides (cf. Milligan et al., ibid.). Hydrophobic modifications at the 5-position of pyrimidine bases, as well as a number of purine modifications have been shown to produce enhanced binding to target sequences (cf. Milligan et al., ibid.). These modified bases include 5-fluorouridine, 5-bromouridine, 5-propynyluridine, 5-bromocytidine, 5-methylcytidine, 5-propynylcytidine, 2-aminoadenine, 7-deazaguanine, 7-deazaguanine and $N^2$-imidazolylpropylguanine.

The uses of the present invention are myriad. One use would be to replace pre-labeling in most applications involving hybridization arrays due to simplicity, potential improved detectability, and lower cost. In general, any application is contemplated where it is desirable to use fluorescent, non-covalently bound nucleic acid stains to identify hybridized probes in arrays of probes on glass substrates.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described and accordingly, all suitable modifications and equivalents may be resorted to, falling within the scope of the invention.

What is claimed is:

1. A method for staining immobilized nucleic acids, comprising the steps of:

providing a microchip structure including a solid substrate having at least one channel disposed thereon;

affixing at least one DNA probe to said solid substrate;

causing target DNA material to move through said at least one channel into proximity with said at least one DNA probe, whereby the target DNA can hybridize with said at least one DNA probe; and causing a fluorescent dye to move through said at least one channel into proximity with hybridized target DNA, whereby the fluorescent dye binds to the hybridized DNA to enable subsequent detection of fluorescence, at least one of said target DNA material and said fluorescent dye being caused to move through said at least one channel under the influence of an externally applied electric potential.

2. A method according to claim 1, wherein said at least one DNA probe is affixed within at least one channel contained in said substrate the target DNA, fluorescent dye and further reagents and transported through the channel.

3. A method according to claim 2, wherein the target DNA is caused to move by applying electric potentials across said at least one channel so as to impart electroosmotic or electrophoretic movement of the target DNA into proximity with said at least one probe.

4. A method according to claim 2, wherein the fluorescent dye is caused to move by applying electric potentials across said at least one channel so as to impart electroosmotic or electrophoretic movement of the fluorescent dye into proximity with said at least one probe.

5. A method according to claim 2, wherein the target DNA and the fluorescent dye are both caused to move by applying electric potentials across the channels in a distribution designed to impart electroosmotic or electrophoretic movement of the target DNA and the fluorescent dye into proximity with said at least one probe.

6. A method according to claim 1, wherein the step of moving fluorescent dye includes applying hydraulic pressure to said at least one channel in a manner designed to impart movement of the fluorescent dye into proximity with said at least one probe.

7. A method according to claim 1, wherein the step of moving target DNA includes applying hydraulic pressure to said at least one channel in a manner designed to impart movement of the target DNA into proximity with said at least one probe.

8. A method as claimed in claim 1, wherein said at least one DNA probe is affixed to said at least one channel substantially throughout the length of said at least one channel.

9. A method as claimed in claim 8, wherein multiple different probes are affixed to said at least one channel of the microchip structure.

10. A method as claimed in claim 9, wherein each of at least two of said multiple different probes is affixed to a discrete site within said at least one channel.

11. An apparatus for staining and detecting immobilized nucleic acids, comprising:
a solid substrate having at least one channel disposed thereon and adapted to have at least one DNA probe affixed thereto;
means for moving target DNA material through said at least one channel and into proximity with said at least one DNA probe, whereby the target DNA hybridizes with said at least one DNA probe;
means for moving a fluorescent dye through said at least one channel and into proximity with hybridized target DNA, whereby the fluorescent dye binds to the hybridized DNA to enable subsequent detection of fluorescence, at least one of said means for moving target DNA material and said means for moving a fluorescent dye comprising an externally applied electric potential; and
means for detecting fluorescence of the hybridized, dye-bound DNA at the site of hybridization in said channel.

12. An apparatus according to claim 11, wherein the substrate has a channel pattern which includes a plurality of channels through which the target DNA and the fluorescent dye move.

13. An apparatus according to claim 12, wherein the means for moving target DNA includes means for applying an electric potential across the channels in a distribution designed to impart electroosmotic or electrophoretic movement of the target DNA into proximity with said at least one probe.

14. An apparatus according to claim 12, wherein the means for moving fluorescent dye includes means for applying an electric potential across the channels in a distribution designed to impart electroosmotic or electrophoretic movement of the fluorescent dye into proximity with the probes.

15. An apparatus according to claim 12, wherein the means for moving both the target DNA and the fluorescent dye includes means for applying an electric potential across the channels in a distribution designed to impart electroosmotic or electrophoretic movement of the target DNA and the fluorescent dye into proximity with the probes.

16. An apparatus according to claim 11, wherein the means for moving target DNA includes means for applying a hydraulic force to said at least one channel at a level sufficient to impart movement of the target DNA into proximity with said at least one probe.

17. An apparatus according to claim 11 wherein the means for moving fluorescent dye includes means for applying a hydraulic force to said at least one channel at a level sufficient to impart movement of the fluorescent dye into proximity with said at least one probe.

18. An apparatus according to claim 1, wherein said at least one DNA probe is affixed to said at least one channel substantially throughout the length of said at least one channel.

19. An apparatus according to claim 18, wherein multiple different probes are affixed to said at least one channel.

20. An apparatus according to claim 19, wherein each of at least two of said multiple different probes is affixed to a discrete site within said at least one channel.

21. A method for staining and detecting immobilized nucleic acids, comprising the steps of:
providing a microchip structure including a solid substrate having at least one channel contained therein, and at least one DNA probe affixed within said at least one channel;
flowing a carrier solution comprising target DNA material through said at least one channel and into proximity with said at least one DNA probe, whereby the target DNA hybridizes with specific ones of said at least one DNA probe;
moving a fluorescent dye through said at least one channel and into proximity with the hybridized target DNA, whereby the fluorescent dye binds to the hybridized DNA to enable subsequent detection of fluorescence;
washing to remove excess fluorescent dye; and
detecting the fluorescence of the hybridized, stained DNA.

22. A method according to claim 21, wherein the step of moving target DNA includes applying electric potentials across said at least one channel in a distribution designed to impart electroosmotic or electrophoretic movement of the target DNA into proximity with said at least one probe.

23. A method according to claim 21, wherein the step of moving fluorescent dye includes applying electric potentials across said at least one channel in a distribution designed to impart electroosmotic or electrophoretic movement of the fluorescent dye into proximity with said at least one probe.

24. A method according to claim 21, wherein the step of moving fluorescent dye includes applying hydraulic pressure to said at least one channel in a manner designed to impart movement of the fluorescent dye into proximity with said at least one probe.

25. A method according to claim 21, wherein the step of moving target DNA includes applying hydraulic pressure to said at least one channel in a manner designed to impart movement of the target DNA into proximity with said at least one probe.

26. A method for staining immobilized target material, comprising the steps of:

providing a microchip structure including a solid substrate having at least one channel disposed thereon;

affixing at least one probe to said solid substrate; and simultaneously causing target material to move through said at least one channel into proximity with said at least one probe and causing a fluorescent dye to move through said at least one channel into proximity with the hybridized target material, whereby the target material hybridizes with said at least one probe, and the fluorescent dye binds to the hybridized material to enable subsequent detection of fluorescence, at least one of said target material and said fluorescent dye being caused to move through said at least one channel under the influence of an externally applied electric potential.

27. A method according to claim 26, wherein said at least one probe are DNA probes and the target material is target DNA material.

28. A method according to claim 26, wherein the step of simultaneously moving target material and the fluorescent dye through said at least one channel includes application of hydraulic force to said at least one channel.

29. A method according to claim 26, further comprising, prior to the step of simultaneously moving the target material and the fluorescent dye through said at least one channel, mixing the target material and the fluorescent dye together.

30. A method according to claim 26, further comprising, after the step of simultaneously moving the target material and the fluorescent dye through said at least one channel, washing the solid substrate to remove unbound target material and dye.

31. A method according to claim 26, wherein said at least one probe are RNA probes and the target material is target RNA material.

32. A method according to claim 26, wherein said at least one probe are oligodeoxynucleotides.

33. A method according to claim 26, wherein said at least one probe are oligoribonucleotides.

34. A method according to claim 26, wherein said at least one probe are peptide nucleic acids.

35. A method according to claim 26, wherein said at least one probe are oligonucleotide analogues.

36. A method according to claim 35, wherein the oligonucleotide analogues contain a modified internucleotide linkage.

37. A method according to claim 36, wherein the internucleotide linkage is selected from the group consisting of phosphotriester, phosphorothioate, phosphorodithioate, methylphosphonate, phosphoramidate, carbonate, carboxymethyl, acetamidate, carbamate, peptide, thioether, sulfonate, sulfonamide, sulfamate, sulfide, sulfoxide, sulfone, formacetal, thioformacetal, methylhydroxylamine, N-cyanoguanidine and alkylsilyl linkages.

38. A method according to claim 35, wherein the oligonucleotide analogues contain a modified sugar.

39. A method according to claim 38, wherein the modified sugar is selected from the group consisting of 2'-halo, 2'-O-alkyl and 2'-O-allyl ribose sugars.

40. A method according to claim 35, wherein the oligonucleotide analogues contain a modified heterocyclic base.

41. A method according to claim 40, wherein the modified heterocyclic base is selected from the group consisting of 5-fluorouridine, 5-bromouridine, 5-propynyluridine, 5-bromocytidine, 5-methylcytidine, 5-propynylcytidine, 2-aminoadenine, 7-deazaguanine, 7-deazaguanine and $N^2$-imidazolylpropylguanine.

* * * * *